United States Patent [19]

Weston

[11] Patent Number: 4,963,351

[45] Date of Patent: Oct. 16, 1990

[54] SHAVING AID

[75] Inventor: William Weston, Wayne, N.J.

[73] Assignee: BHN Associates, Wayne, N.J.

[21] Appl. No.: 456,940

[22] Filed: Dec. 26, 1989

[51] Int. Cl.$^5$ .............................................. A61K 7/15
[52] U.S. Cl. ...................................... 424/73; 514/873;
 252/135
[58] Field of Search .......................... 424/73; 514/873;
 252/135

[56] References Cited

U.S. PATENT DOCUMENTS

| | | | |
|---|---|---|---|
| 2,085,733 | 7/1937 | Bird | 167/85 |
| 3,705,855 | 4/1972 | Marschner | 252/90 |
| 3,966,627 | 6/1976 | Gray | 252/99 |
| 4,115,308 | 9/1978 | Guerry | 252/135 |
| 4,548,810 | 10/1985 | Zofchak | 424/73 |
| 4,715,979 | 12/1987 | Moore et al. | 252/91 |
| 4,744,979 | 5/1988 | Osipow et al. | 424/73 |
| 4,761,279 | 8/1988 | Khall et al. | 424/73 |
| 4,925,585 | 5/1990 | Strauss et al. | 252/89.1 |

FOREIGN PATENT DOCUMENTS 142762 9/1935 Australia .
771613 11/1967 Canada .
470918 8/1937 United Kingdom .

OTHER PUBLICATIONS

Cosmetic Materials, vol. II, pp. 330–337 and 352 (1963), Merch—9th Ed. Abs. 8283, pp. 1103–1104(1976).

Primary Examiner—Thurman K. Page
Assistant Examiner—James M. Spear
Attorney, Agent, or Firm—Albert L. Gazzola; Carl P. Steinhauser

[57] ABSTRACT

A water-soluble particulate composition of free-flowing solids suitable for use in wet shaving which comprises, as an essential ingredient, sodium tripolyphosphate hexahydrate, an emollient, and a hydrophilic non-ionic surfactant, and method for preparation of the composition.

6 Claims, No Drawings

SHAVING AID

FIELD OF THE INVENTION

My invention relates to a novel shaving aid suitable for use in wet shaving and capable of prolonging the useful life of the cutting edge at a razor used to easily remove whiskers even with very hard water.

BACKGROUND OF THE INVENTION

Long prior to King Camp Gillette's invention of the safety razor and long prior to his contemporary Charles Dana Gibson's creation of the clean-shaven "Gibson Man", to complement his better known "Gibson Girl", man has been wet shaving with a blade and softening his beard and face by the use of either a soap or a soap preparation. Of course, it goes without saying that to this date wet shaving is still, by far, the preferred method of removing whiskers, albeit electric razors have made their way into the marketplace with commendable success.

Wet shaving by lathering with a soap or a soap preparation is by no means without its drawbacks. For example, so-called hard water often interferes with the lathering and beard-softening properties of soap by forming insoluble calcium salts of the fatty acid component of soap and by curdling the lather. Of course, curdling cakes the razor and the sink (wash basin) making removal of the lather that much more difficult.

Despite advances and improvements in electric or dry shavers, many people prefer to remove hair, facial for men, legs and underarm for women, using a blade, shaving cream and water primarily because it is believed that a closer cut of the unwanted hair is achieved.

Despite the improvements in shaving creams, razors tend to become dull rather quickly especially due to hard water which is generally found throughout the world. Although such shaving creams are formulated to produce a rich lather, and contain emollients and fragrances to soothe the skin and impart a more desirable fragrance, they do not overcome the basic problem caused by hard water, supra. Commercial water softeners which functionally sequester hardness-causing components in water (e.g., $CaCO_3$) are not always within the reach, financially, of certain of the shaving public. Certain regions of the United States of America have, on the average, up to about 500 and more parts per million (ppm) hardness-causing components in their tap water than other regions of this country. For example, while the New England area has weighted average tap water hardness of about 30 ppm, states bordering the Great Lakes have a weighted average of about 175 ppm.

It follows, also, that an improperly cleansed razor blade, which still has caked lather on it, will lose its delicate sharp edge readily by virtue of the corrosive nature of soap and soap preparations. Hence, the initial desirable razor slip property of a new blade readily gives way to razor drag, necessitating frequent changes of blades. This, obviously, substantially increases the cost of wet shaving.

Interest has, in the past, concentrated on: better metals for razor blades, bonded blades, twin-edge bonded blades, improved shaving creams, pre-shave lotions, etc., all the while tolerating the aforementioned difficulties attending the use of soaps and soap preparations. In short, nothing really innovative relative to wet shaving with a blade has surfaced.

As will be seen hereinafter, I have discovered what, in my judgment, is a unique shaving aid.

PRIOR ART

As shown hereinafter, a new approach was attempted using, as an essential element of a wet shaving aid, sodium tripolyphosphate hexahydrate. A search of the prior art uncovered some art such as, U.S. Pat. No. 3,966,627 to Gray and U.S. Pat. No. 4,115,308 to Guering.

The Gray patent describes a cleaning composition for automatic dishwasher employing inter alia sodium tripolyphosphate hexahydrate as a water-soluble builder salt and as an essential ingredient aluminum silicate for inhibiting overglaze attack. Needless to say, aluminum silicate for this or any other purpose is undesirable in a shaving cream and, therefore, is not formulated in shaving cream preparations.

The Guerry patent discloses alkaline silicate-containing paste form detergent compositions and may contain sodium tripolyphosphate as a water softener and cleaning agent. The silicate, e.g. sodium silicate appears to be an essential ingredient in all of the detergent compositions described by Guerry.

Other references found were:

| | | |
|---|---|---|
| Marschner | 3,705,855 | December 12, 1972 |
| Feigl, et al. (Austrian) | 142,762 | September 10, 1935 |
| Kritchevsky (British) | 470,918 | August 23, 1937 |
| Lanzet (Canadian) | 771,613 | November 14, 1967 |

Marschner, teaches an aerosol composition useful as a cleaning agent or shaving cream which contains sodium tripolyphosphate, an emollient, water and a surfactant in proportions quite afield from the critical percentages hereinbefore set out. In addition, the components are by no means singled out as specifically as they are herein.

Feigl, et al., discloses a shaving soap containing phosphates but by no means suggests the composition of the present invention.

Kritchevsky, relates to a brushless shaving cream which is a plastic emulsion comprising solid higher fatty acid, soap, water and a minor amount of a chemical compound having oleophilic and hydrophilic groups, such as sulphonated castor oil, butyl sulpholeic acid and ester-like derivatives of fatty acids and ethyl hydrogen sulphate. Quite obviously, this is a far cry from the compositions of the present discovery.

Lanzet is directed to aerosol compositions dispensed as a foam and utilized to lubricate human skin prior to the use of an electric shaver. The compositions contain water and alcohol as a vehicle to which is added water-soluble surfactant and a lubricant. Typical lubricants are diesters of dibasic acids having 3 to 10 carbon atoms, the alcohol radical of said esters having 1-4 carbon atoms and diesters of monobasic acids having from 2-8 carbon atoms, the alcohol radical of said esters having from 3-8 carbon atoms. Again, this is by no means the composition of the instant discovery, and neither does it suggest same.

In none of the prior art of which applicant is aware is the problem of water hardness addressed with the resulting dulling of the razor blade.

It is an object of my invention to provide a new and unique wet shaving aid which prolongs the life of a razor blade.

It is a further object of my invention to provide a new and unique wet shaving aid which combats water hardness and facilitates wet shaving.

Another object of my invention is to provide a new and unique wet shaving aid which avoids curd forming on the razor blade as a result of insoluble calcium salts formed with fatty components of the soap.

A still further object of my invention is to eliminate as much curd as possible on the wash basin which results in connection with wet shaving.

Because the razor need not be cleaned by running water after each run, it is an object of this invention to save water.

These and further objects and advantages of my invention will appear as this specification progresses.

SUMMARY OF THE INVENTION

The present invention relates to a truly different shaving aid. More particularly, the instant discovery concerns a free-flowing solids composition which readily dissolves in water and which, when dissolved in water and the resulting solution applied to the skin, provides a superior beard and skin softener without the resultant dryness and aforementioned other disadvantages attendant the use of conventional shaving soaps and creams, for example. In short, no shaving soap, cream or gel is needed, thus obviating the attendant need to remove excess conventional shaving aid by washing and/or rinsing the skin following shaving. Quite unexpectedly, only a very small quantity of the novel composition is required per shave, as will be seen infra. Furthermore, it is a complete product in that it contains all the necessary ingredients for pre-and-post-shaving in one formula.

Of course, one may use the just mentioned conventional shaving aid conjointly with that of the present invention. It must be emphasized that conjoint use is absolutely unnecessary for even the toughest beards.

Still more particularly, the present invention concerns a water-soluble particulate composition of free-flowing solids suitable for use in wet shaving consisting essentially of:

(i) from about 78% to about 87% sodium tripolyphosphate hexahydrate;
(ii) from about 9% to about 16% emollient; and
(iii) from about 0.5% to about 3% hydrophilic non-ionic surfactant, the above percentages for components (i)–iii) being by weight based upon the total weight of the composition.

Preferably, the sodium tripolyphosphate hexahydrate, emollient and the hydrophilic non-ionic surfactant are present in the following concentrations:

(i) from about 80% to about 85%;
(ii) from about 11.5% to about 14%; and
(iii) from about 1.25% to about 2.5%.

Sodium tripolyphosphate ($Na_5P_3O_{10}$) is a well known commercial granular detergent builder and, surprisingly enough, it can be hydrated to sodium tripolyphosphate hexahydrate ($STP \cdot 6H_2O$) and still retain its crisp, free-flowing properties. Stoichiometric hydration occurs, i.e., no less than 6 moles of $H_2O$ combine with 1 mole of STP. Partial hydration means not all the STP is hydrated; it does not signify less than the ratio of 6:1.

Theoretically, 29.4 pounds (lbs.) of water can be added to 100 lbs. of anhydrous STP to give 129.4 lbs. of $STP \cdot 6H_2O$. However, most commercial STP is less than 100% pure. A product containing 19–20% water is very possible on a regular basis.

For the purpose of the present invention, at least about 15% $H_2O$ is required to complete hydration, i.e., $$\frac{29.4 \text{ lbs.}}{129.4 \text{ lbs.}} \times 100 = 22.7\% \text{ H}_2\text{O}.$$

Several advantages to higher percentages of hydration are:

(i) enhanced absorbency of emollients and surfactants, as well as optional components which will be discussed infra;
(ii) improved solution rate in water;
(iii) decreased tendency to cake;
(iv) retention of free-flowing properties of STP $H_2O$ in granular or powdered form;
(v) ability to withstand different conditions of humidity, storage and use due to reduced hygroscopicity;
(vi) minimized heat of hydration when dissolved in water; and
(vii) decreased tendency to decompose (dehydrate) to ortho- and pyrophosphate.

Hydration of STP requires special blending in order to reduce fines and to avoid caking or lumping, as will be seen hereinafter. Quick hydration and ready removal of the heat of hydration are important to preclude said caking or lumping. U.S. Pat. No. 2,046,092 to Montague, teaches contacting, with agitation, the STP with water in the form of ice.

The preferred cosmetic emollient in the shaving aid composition of the present invention is mineral oil, especially white mineral oil. Use of other emollients is contemplated, however, though preferably in combination with white mineral oil.

Typical other emollients are: esters of long chain fatty acids, such as, for example, isopropyl myristate, ethyl palmitate, isopropyl stearate, isopropyl palmitate, methyl oleate, and the like; natural fats, such as coconut, cocoa butter, soybean oils and the like; sorbitol; and glycerine. If desired, two or more emollients may be used in the same composition.

Illustrative hydrophilic non-ionic surfactants suitable for use in the shaving aid compositions of the instant discovery are long-chain fatty acid esters derived from ethylene oxide or polyhydric alcohols, such as glycols, polyglycols, glycerol, sorbitol or sucrose, ethers of long-chain fatty alcohols, alkylated phenols prepared by direct reaction with ethylene oxide and the like. Typical are polyethylene glycol monolaurate, polyethylene glycol dilaurate, polyethylene glycol monooleate, polyethylene glycol dioleate, polyoxyethylene (40) monostearate, polyoxyethylene (20) sorbitan monopalmitate, polyoxyethylene (20) sorbitan monostearate, polyoxyethylene (20) sorbitan monooleate, and other like water-soluble members of the "Tween"[1] series of surface-active agents which are polyoxyethylene derivatives of fatty acid partial esters of sorbitolanhydrides. Of course, mixtures of the water-soluble, non-ionic surfactants of the type contemplated herein, of which the above-listed are merely illustrative, may be used in the ratio hereinabove given.

[1] "Tween" is the trademark of Atlas Chemical Industries, Inc. for its water-soluble series of surface active agents.

Any acceptable F. D. & C. dye, D. & C. inorganic or organic coloring materials, dyes, pigments, etc., or combinations of such dyes, may be used as a colorants to improve the appearance of the composition. When used, from 0.001 to 2 parts by weight is added to the composition.

Similarly, any acceptable fragrance, such as lavender, lime or lemon scents, may be used. When used, from 0.01 to 5 parts by weight of the fragrance may be added to the composition.

Other optional additives include minor amounts up to about 1.5% anti-allergens such as, o-alkyl-trimethylammonium chloride substituted anhydroglucose, also known as Polymer JR, a trademark of Union Carbide Corporation (UCC). Scientists with this company have good reason to believe that Polymer JR is substantive to the skin and that it "produces its effect by penetrating into the outer layers of the stratum corneum, thus helping that membrane to maintain its integrity". Faucher, et al. "Cosmetics and Toiletries", (1977), Vol. 92, No. 6, page 39.

If desired, minor amounts, up to about 1.5% of a low viscosity dimethicone (dimethylsiloxane polymer) may be incorporated into the present invention composition to enhance razor slip with resultant skin protection.

Optionally, also other additives, such as hydrophilic, water-soluble colloids may be present in minor amounts up to about 1.5%. Typical are the propylene glycol alginate products marketed under the trademark Kelcoloid by Merck & Co., Inc.

Hydration of the STP reactant according to the present invention involves special conditions in order to achieve the high water concentrations hereinbefore recited. Pursuant to a preferred embodiment, 1,680 lbs. of light density STP granules is charged to a rotary type blender with inner baffles which move the charge from the charge end of the blender to the discharge end thereof. Typical is a Munson Blender manufactured by the Munson Machinery Company, Inc., Utica, N.Y., which has a 75-cubic-foot operating capacity (150 cu. ft. overall blending chamber). Upon starting the Munson Blender up, which rotates at the rate of about 15 revolutions per minute (rpm) and is at ambient temperature when being fed the STP reactant, water having a temperature of about 3° C.–5° C. is sprayed onto the surface of the tumbling STP at the rate of 5.0 gallons per minute @20 psig.

A total of 525 gallons of $H_2O$ is added during the first 15 minutes of blending. When the first 5 gallons has been added, it is necessary to control the heat of hydration to about 60° C.–65° C. throughout continued blending.

When all the ice cold $H_2O$ has been added, blending is continued for about 5 minutes, at which time another 620 lbs. of STP is added to the reaction mixture while blending continues. Mixing is continued for 45 minutes more while maintaining the heat of hydration at a temperature of about 60° C.–65° C. and in order to essentially complete hydration.

Following these procedural steps, product sodium tripolyphosphate hexahydrate (STP.6$H_2O$) containing about 17%–22% $H_2O$ by weight is removed from the blender where it is allowed to cure overnight or for a minimum of 12 hours.

The temperature of the reaction mixture is maintained, as indicated above, between about 60° C. and about 65° C. throughout the reaction cycle following the addition of the first 5 gallons of water out of a total 525 gallons of $H_2O$. Of course, hot vapors are vented from the reaction chamber during reaction.

Should venting, per se, be inadequate to maintain reaction temperature due to elevated ambient temperatures, for instance, it has been found very desirable to reduce the temperature of the reacting mixture by blowing cool air into the chamber in order to achieve and maintain the 60° C.–65° C. reaction temperature. For this purpose, the heated vapors in the chamber resulting from the exothermic reaction may be drawn out, cooled in, say, an air conditioning unit, and returned to the reaction chamber at a temperature sufficient to maintain the reaction temperature at the desired level.

For example, hot vapors drawn from the reaction chamber can be cooled to about 13° C., say, under many circumstances and directed into the reaction chamber of the volume hereinbefore described (Munson Blender) and generally control the exothermic heat of reaction and allow hydration to take place at a uniform temperature of about 60° C.–65° C.

As suggested above, excessively hot or excessively cold ambient temperatures about the blender require compensating adjustments to the just described illustrative embodiments for maintaining the heat of hydration within the range of about 60° C.–65° C.

Product STP.6$H_2O$ produced according to the above-described hydration process and containing about 17%–22% $H_2O$, by weight, can be used to prepare an excellent shaving aid in accordance with the present invention and having the very desirable properties described supra. The following examples are merely illustrative and not intended to limit the invention unduly.

| Components | EXAMPLES Percentages by weight |
|---|---|
| EXAMPLE I | |
| Sodium tripolyphosphate hexahydrate (sodium hexametaphosphate) | 85.0000 (78% STP.18% $H_2O$) |
| Klearol (white mineral oil) | 10.0000 |
| Polymer JR | 0.5000 |
| Isopropyl palmitate | 0.5000 |
| Dow Corning 200 Fluid | 1.0000 |
| PEG 400 dioleate | 0.5000 |
| Fragrance | 1.0000 |
| Dye FD & C Blue #1 | 1.0000 |
| $H_2O$ | 0.5000 |
| | 100.0000 |
| EXAMPLE II | |
| Sodium tripolyphosphate hexahydrate | 81.0850 (78% STP.22% $H_2O$) |
| Klearol (white mineral oil) | 12.0000 |
| PEG 400 dilaurate | 1.5000 |
| Isopropyl palmitate | 1.0000 |
| Polymer JR | 1.0000 |
| Kelcoloid HVF | 1.0000 |
| Fragrance | 2.0000 |
| Dye FD & C Blue #1 | 0.0150 |
| $H_2O$ | 0.4000 |
| | 100.0000 |
| EXAMPLE III | |
| Sodium tripolyphosphate hexahydrate | 87.0000 (83% STP.17% $H_2O$) |
| Klearol (white mineral oil) | 7.0000 |
| Isopropyl myristate | 2.0000 |
| Polyoxyethylene (20) sorbitan monopalmitate | 3.0000 |
| Polymer JR | 0.2000 |
| Dimethicone | 0.1000 |
| Fragrance | 0.1800 |
| Dye FD & C Blue #1 | 0.1200 |
| $H_2O$ | 0.4000 |
| | 100.0000 |

EXAMPLES

| Components | Percentages by weight |
|---|---|
| EXAMPLE IV | |
| Sodium tripolyphosphate hexahydrate | 83.0000 (80% STP.20% H$_2$O) |
| Klearol (white mineral oil) | 9.0000 |
| Coconut oil | 3.0000 |
| Polyoxyethylene (40) monostearate | 1.5000 |
| Polyoxyethylene (20) sorbitan monolaurate | 1.5000 |
| FD & C Blue #1 | 0.2000 |
| Dimethicone, low viscosity | 1.5000 |
| Mixture of linoleic acid & proline | 0.5000 |
| H$_2$O | 0.3000 |
| | 100.0000 |
| EXAMPLE V | |
| Sodium tripolyphosphate hexahydrate | 79.0000 (81% STP.18.5% H$_2$O) |
| Klearol (white mineral oil) | 13.0000 |
| Soybean oil | 2.0000 |
| Polyoxyethylene (20) sorbitan monooleate | 1.5000 |
| Polyoxyethylene glycol monolaurate | 1.5000 |
| Polymer JR | 1.4000 |
| Fragrance | 0.2000 |
| Dye FD & C Blue | 0.8000 |
| H$_2$O | 0.6000 |
| | 100.0000 |
| EXAMPLE VI | |
| Sodium tripolyphosphate hexahydrate | 81.950 (78% STP.22% H$_2$O) |
| Klearol (white mineral oil) | 8.000 |
| Polymer JR | 1.000 |
| Isopropyl palmitate | 1.000 |
| Fragrance | 2.000 |
| Isostearamidopropyl dimethylamine lactate | 3.000 |
| Polyethylene glycol 400 dilaurate | 3.000 |
| FD & C Blue #1 | 0.001 |

The above formula appears to be a preferred shaving composition

On an average, the pH (1% aqueous solution) of the shaving aid formulation prepared according to the present invention is in the range of about 9.8 to about 10.2.

The water-soluble particulate compositions of free-flowing solids, prepared as described above, are extremely easy to use as shaving aids:

1. Pour approximately one heaping teaspoonful of the composition into conventional bathroom sink and half fill with water to the temperature desired.[2]
2. Swish lightly to dissolve and distribute the product in water.
3. Prep face by washing with the product or by just patting the beard and then lightly rubbing the product solution into the beard.
4. Swish razor in the solution and continue to do so to rinse the razor off while shaving, and when shaving is completed. It is advantageous not to rinse off the razor under tap water after the final rinse, since the residual product composition remaining on the razor's edge provides excellent protection of the edge upon storage. The protection is attributable to the nature of the product composition with its emollient/surfactant components which provide a protective lubricant film, thus guarding against oxidation of the cutting

[2] Ca. ½-gallon, on the average. edge. Obviously, any blade so protected retains its cutting edge much longer.

5. For most the same reasons advanced in paragraph 4, just above, it is advantageous to rinse off the face with the product solution after shaving, rather than using tap water. In other words, the emollient/surfactant components have a "moisturizing" effect most beneficial to parties with dry skin.

It is important to here point out that the compositions of the instant discovery perform equally well for ladies. The same directions apply with respect to the use of the product in a bathroom sink in order to milady shave her legs.

As suggested hereinbefore, the components of the shaving aid described herein at once soften hard water, assist in preserving the life of the razor blade, moisturize the skin; and—due to the superior cleansing properties of STP—eliminate "sink ring" and "bathtub ring", even in cold water. Of course, the procedure for using the compositions as an aid to shaving inherently saves energy by obviating the practice of running hot tap water during the shaving process. In addition, the emollients in the compositions heretofore described impart excellent "feel" to the skin during and after shaving and reduce so-called "razor drag". Incorporating, optionally, dimethicone not only enhances "razor slip" but cooperates with the emollient/surfactant components in avoiding razor corrosion. Of course, the heretofore-mentioned enhanced absorbency of emollients, surfactants and the STP.6H$_2$O of the present invention is a critical factor in producing the many desirable properties above discussed.

While the intention has been described with specific references and examples, other modifications will be readily apparent to those skilled in the art.

What is claimed is:

1. A water-soluble particulate composition of free-flowing solids suitable for use in wet shaving consisting essentially of:
   (i) from about 78% to about 87% sodium tripolyphosphate hexahydrate containing about 15% to about 22.7% water by weight;
   (ii) from about 9% to about 16% mineral oil emollient;
   (iii) from about 0.5% to about 3% hydrophilic non-ionic surfactant, and
   (iiii) up to about 1.5% of a low viscosity dimethicone, the above percentages for components (i)-(iiii) being by weight based upon the total weight of the composition.

2. The composition of claim 1 wherein components (i)-iii) are present in the following concentrations:
   (i) from about 80% to about 85%;
   (ii) from about 11.5% to about 14%; and
   (iii) from about 1.25% to about 2.5%.

3. The composition of claim 1 wherein the sodium tripolyphosphate hexahydrate contains from about 17% to about 22% water, by weight.

4. The composition of claim 3 wherein the emollient is white mineral oil.

5. The composition of claim 4 wherein the non-ionic hydrophilic surfactants are selected from the group consisting of long-chain fatty acid esters derived from ethylene oxide or polyhydric alcohols, ethers of long-chain fatty alcohols and poloxyethylene derivatives of fatty acid partial esters of sorbitol anhydrides.

6. The composition of claim 3 wherein up to about 1.5% by weight of a low viscosity dimethicone is present in the composition.

* * * * *